United States Patent [19]

Becker

[11] Patent Number: 5,017,705

[45] Date of Patent: May 21, 1991

[54] PRODUCTION OF 3,5,6-TRICHLOROPYRIDIN-2 OL AND NOVEL INTERMEDIATES THEREOF

[75] Inventor: Yigal Becker, Tel Aviv, Israel

[73] Assignee: Luxembourg Industries (Pamol) Ltd., Israel

[21] Appl. No.: 348,983

[22] Filed: May 8, 1989

[30] Foreign Application Priority Data

May 11, 1988 [IL] Israel ......................................... 86341

[51] Int. Cl.$^5$ ........................................... C07D 213/64
[52] U.S. Cl. .................................... 546/250; 546/300; 546/303; 546/345; 558/368; 558/398; 558/440; 558/441
[58] Field of Search ................ 558/398, 440, 441, 368; 546/303, 300, 345, 250

[56] References Cited

U.S. PATENT DOCUMENTS

| | | | |
|---|---|---|---|
| 3,007,931 | 11/1961 | Simpson et al. .................... | 558/440 |
| 4,245,098 | 1/1981 | Steiner et al. ...................... | 546/250 |
| 4,327,216 | 4/1982 | Martin ................................ | 546/250 |
| 4,360,676 | 11/1982 | Martin et al. ...................... | 546/243 |
| 4,435,573 | 3/1984 | Lysenko ............................. | 546/250 |
| 4,465,186 | 5/1987 | Steiner .............................. | 558/440 |
| 4,468,354 | 8/1984 | Lysenko ............................. | 546/250 |
| 4,469,896 | 9/1984 | Steiner .............................. | 568/495 |

*Primary Examiner*—Mary C. Lee
*Assistant Examiner*—Jacqueline Haley
*Attorney, Agent, or Firm*—Steinberg & Raskin

[57] ABSTRACT

Novel aryl and heteroaryl 4-cyano-2,2,4-trichlorobutyrates are prepared by reacting a corresponding aryl or heteroaryl trichloroacetate with acrylonitrile in the presence of a catalyst. Also provided is a novel process for producing 3,5,6-trichloropyridin-2-ol comprising cyclization of an aryl or heteroaryl 4-cyano-2,2,4-trichlorobutyrate in an inert organic solvent at elevated temperatures, in the presence of anhydrous hydrogen chloride.

20 Claims, No Drawings

PRODUCTION OF 3,5,6-TRICHLOROPYRIDIN-2 OL AND NOVEL INTERMEDIATES THEREOF

BACKGROUND OF THE INVENTION

The present invention relates to a process and novel intermediates for the production of 3,5,6-trichloropyridin-2-ol and salts thereof. These compounds are useful as intermediates in the manufacture of various herbicides, fungicides and insecticides, for example, the important insecticide 0,0-diethyl-0-3,5,6-trichloro-2-pyridyl phosphorothioate, (U.S. Pat. No. 3,244,586).

Various processes are known for the production of 3,5,6-trichloropyridin-2-ol. For example, it can be prepared by high temperature chlorination of 6-bromo or 6-chloro-2-ethoxypyridine [Recueil Trav. Chim. 70, 182 (1951)] or of 6-chloro-2-methoxypyridine (European Pat.No. 0,124,657).

3,5,6-Trichloropyridin-2-ol can also be prepared by basic hydrolysis of 2,3,5,6-tetrachloropyridine [Recueil Trav. Chim. 70, 182 (1951); Japanese Pat. No. 58-154-561]. The 2,3,5,6-tetrachloropyridine starting material can be prepared, for example, by high temperature vapor phase chlorination of pyridine or pyridine derivatives, such as 2,6-dichloropyridine and 3,5-dichloro-2-trichloromethylpyridine, at temperatures ranging from 200° to 600° C. or by high-temperature chlorination of glutaric acid dinitrile (400°–600° C.), ε-caprolactam or cyclohexanone oxime. These high temperature processes are usually non-selective, producing also other highly chlorinated by-products which must be separated. One such by-product is 2,3,4,5,6-pentachloropyridine which, however, can be converted to the desired tetrachloropyridine by selective reduction of the chlorine atom in the 4-position of the pyridine nucleus (U.S. Pat. Nos. 3,993,654; 3,694,322). Another European Pat. No. 0030215 describes a process for the preparation of 3,3,5-trichloroglutaric acid imide and its subsequent conversion to 2,3,5,6-tetrachloropyridine.

Israel Pat. No. 61581 describes a process whereby a mixture of 2,3,5,6-tetrachloropyridine and 2,3,5-trichloropyridin-2-ol is obtained by reacting trichloroacetyl chloride and acrylonitrile in a solvent at ca 170° C. using various metal compounds as catalysts (yields were not reported).

One of the objects of the present invention is to provide a novel process for the selective production of 3,5,6-trichloropyridin-2-ol in high yield, free from undesired chlorinated pyridine by-products. Such process should lend itself to large-scale industrial application in an economically feasible manner and should present only minimal ecological hazards.

Further objects of the present invention are to provide novel intermediates for use in the above process and to further provide simple and efficient processes for preparing those novel intermediates.

DESCRIPTION OF THE INVENTION

The present invention achieves its primary object by providing a novel process for producing 3,5,6-trichloropyridin-2-ol and alkali metal and alkaline earth metal salts thereof, which comprises cyclizing an aryl 4-cyano-2,2,4-trichlorobutyrate of the general formula

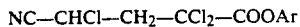     (I)

wherein Ar represents an optionally substituted aryl or heteroaryl radical, by heating the compound of formula (I) at a temperature from about 100° C. to about 180° C., in an inert organic solvent as herein defined, in the presence of anhydrous hydrogen chloride in amounts of from 0.1 to 2 parts by weight per 1 part by weight of the compound of formula (I) and, if desired, converting the 3,5,6-trichloropyridin-ol thus obtained to an alkali metal or alkaline earth metal salt thereof.

The starting materials, i.e. the aryl esters of the formula (I) above are novel and form another aspect of the present invention. The preferred starting materials are those of formula (I) above wherein Ar is a phenyl or naphthyl radical optionally carrying electron-withdrawing substituents, such as Cl and $NO_2$. Especially preferred starting materials of formula (I) above are those in which Ar is a phenyl radical optionally substituted in the para- and/or ortho- position by electron-withdrawing substituents.

The process according to the invention is suitably carried out in a closed glass-lined pressure reactor provided with a stirring arrangement. As stated above, the reaction temperature may range from about 100° C. to about 180° C., the preferred temperature range being 125–135° C.

The inert organic solvent to be used for the cylization of the compounds of formula (I) above, is defined herein as selected from solvents meeting the following requirements:

(a) thermal stability at temperatures within the above mentioned range of 100–180° C.;

(b) chemical inertness towards the starting material of the formula (I);

(c) stability under acidic conditions at the aforementioned temperatures;

(d) a relatively high dielectric constant, preferably higher than 30.

In accordance with the above, examples of suitable solvents for carrying out the process of the invention are alkyl cyanides, particularly those with 2–5 carbon atoms, such as acetonitrile, propionitrile, and also benzonitrile; dialkyl sulfones, such as dimethyl sulfone, alkyl aryl sulfones, alkyl aralkyl sulfones and cyclic sulfones, particularly sulfolane (tetramethylene sulfone). Mixtures of two or more of such solvents can also be suitably used in the process of the invention.

The last-mentioned cyclic sulfone, namely sulfolane, has been found in accordance with the present invention to be most effective and suitable as regards its stability and the high yield, and reaction rate afforded thereby. Its chemical and thermal inertness, high dielectric constant, low vapor pressure, non-toxicity and commercial availability, make sulfolane a unique solvent for the process of the present invention. This finding was totally unexpected in view of the fact that sulfolane has not hitherto been used in a reaction of this type or in any other chemical reaction designed to produce 3,5,6-trichloropyridin-2-ol or 2,3,5,6-tetrachloropyridine.

The presence of dry HCl gas in the reaction medium is essential for effecting the cyclization of the compounds of the formula (I) above. It has been found that the rate of the cyclization reaction is proportional to the ratio of HCl to compound of formula (I) within certain limits. The greater this ratio, the faster is the rate of the reaction. Satisfactory rates were obtained with weight-per-weight ratios of HCl:(I) ranging from 0.1:1 to 2:1, preferably between 0.4:1 and 1:1.

In a typical embodiment of the process according to the present invention phenyl 4-cyano-2,2,4-trichlorobutyrate, a novel compound, is readily and selectively transformed into 3,5,6-trichloropyridin-2-ol by heating the phenyl ester in sulfolane (tetramethylene sulfone) in the presence of anhydrous hydrogen chloride gas at a temperature of 125° C. for about 4–5 hours. After cooling to room temperature, the reaction mixture is found to be homogeneous, free from tars and in particular from the usual 2,3,5,6-tetrachloropyridine by-products and the yield of the desired 3,5,6-trichloropyridin-2-ol is found to be in the range of 70–80%. The reaction is represented in the following reaction scheme:

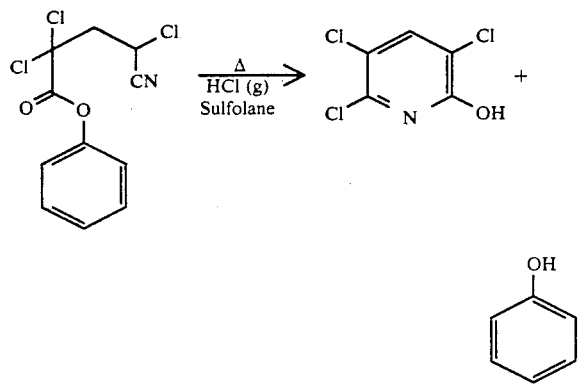

The desired product, 3,5,6-trichloropyridin-2-ol can be isolated from the reaction mixture and separated from the phenolic co-product (ArOH). It has been found in accordance with the present invention that an exceptionally pure product can be isolated in the form of the sodium salt of 3,5,6-trichloropyridin-2-ol, in an extremely simple manner, by selective extraction from an organic phase containing the product with a saturated aqueous solution of sodium carbonate. The sodium salt precipitates in the aqueous sodium carbonate solution and can be readily collected by filtration. The obtained sodium salt of 3,5,6-trichloropyridin-2-ol can be used as such, without further purification, in the phosphorylation reaction to form, e.g. O,O-diethyl-O-3,5,6-trichloro-2-pyridyl phosphorothioate. Alternatively said sodium salt can be acidified with inorganic acids to obtain pure 3,5,6-trichloropyridin-2-ol which in turn can be converted, if desired, to another alkali metal or alkaline earth metal salt.

The phenolic ArOH co-product, formed in the process according to the invention, can advantageously be recovered from the residual reaction solution, subsequent to the isolation of the 3,5,6-trichloropyridin-2-ol sodium salt, by extraction of the organic phase with aqueous sodium hydroxide solution, followed by acidification with an inorganic acid. This recovery of the phenol is desirable both from the ecological aspect and from the economical one, since it can of course be recycled for use in the preliminary production of the starting material of the formula (I) as described hereinbelow. In order to further minimize ecological problems and improve the economics of the process of the present invention, the solvent is also recovered by distillation and recycled into the process.

In accordance with a preferred interesting embodiment of the invention, the starting material of the formula (I) above is the 3,5,6-trichloropyrid-2-yl ester of 4-cyano-2,2,4-trichlorobutyric acid. The use of this novel compound results in an ArOH "co-product" of the process according to the invention which is identical with the desired main product, namely 3,5,6-trichloropyridin-2-ol. As stated above, this product can be easily isolated from the reaction mixture as the sodium salt in high yield and very high purity. A desired portion of the obtained amount of this product can be recycled for use in the preparation of the aforesaid 3,5,6-trichloropyridin-2-ol ester starting material of formula (I).

In accordance with another aspect of the present invention there are provided novel aryl 4-cyano-2,2,4-trichlorobutyrates of the general formula:

$$NC-CHCl-CH_2-CCl_2-COOAr \quad (I)$$

wherein Ar represents an optionally substituted aryl or heteroaryl radical.

In the above formula (I) Ar is preferably a phenyl or naphthyl radical optionally carrying one or more electronwithdrawing substituents, more preferably a phenyl radical optionally substituted in the para- and/or ortho-positions by electron-withdrawing substituents, such as Cl and $NO_2$.

Another preferred compound of formula (I) above is 3,5,6-trichloropyrid-2-yl 4-cyano-2,2,4-trichlorobutyrate.

The novel compounds of formula (I) above can be prepared, in accordance with another aspect of the present invention, by reacting the corresponding aryl ester of trichloroacetic acid of the general formula:

$$Cl_3CCOOAr$$

wherein Ar is as defined above, with acrylonitrile in the presence of a catalytic amount of a metal selected from the main transition metal series and sub-groups IB and IIB or a salt or oxide of such metal, at a temperature from about 80° C. to about 180° C., preferably from about 125° C. to about 150° C.

Several of the aryl trichloroacetate starting materials and their methods of preparation are recorded in the chemical literature. The others can be prepared by analogous methods.

The above process for the preparation of the compounds of formula (I) according to the invention may be conducted in the presence of a suitable polar aprotic solvent, provided that such solvent is inert to the aryl trichloroacetate and acrylonitrile reactants at the reaction temperatures. Preferred solvents are those which are capable of dissolving or forming complexes with the metal salt or oxide catalysts. Examples of suitable solvents for this reaction are alkyl cyanides, particularly those with 2–5 carbon atoms, such as acetonitrile, propionitrile, 3-alkoxypropionitriles such as 3-methoxy- and 3-ethoxypropionitrile and also benzonitrile; aliphatic ketones having 3–8 carbon atoms; dialkyl ethers and cyclic ethers; ethylene glycol dialkyl ethers and diethylene glycol dialkyl ethers; hexamethylphosphoric acid triamides; N,N-dialkylamides of lower alkanoic acids; dialkyl sulfones, such as dimethyl sulfone, alkyl aryl sulfones, alkyl aralkyl sulfones and cyclic sulfones, particularly sulfolane (tetramethylene sulfone), as well as mixtures of such solvents. A particularly preferred solvent is sulfolane for the reasons explained hereinbelow.

The above mentioned reaction of the aryl trichloroacetates with acrylonitrile, to form the compounds of formula (I), is catalyzed by metals selected from the main transition metal series and from sub-groups IB and IIB of the Periodic Table or by salts and oxides thereof. Examples of such catalysts are Cu(O), Cu(I) and Cu(II), Fe(II) and Fe(III) oxides, halides and other salts, such as sulfates, sulfites, sulfides, nitrates, nitrites, carbonates, cyanides etc. The preferred catalysts are cuprous and cupric salts and oxides. The catalysts are used in amounts of 0.1–5 mole %, preferably 2–4 mole %, relative to the acrylonitrile.

As stated above, the preferred solvent for use in the preparation of the compounds of formula (I) is sulfolane because it is also the preferred solvent in the subsequent reaction of cyclizing the compounds of formula (I) above to form the desired 3,5,6-trichloropyrid-2-ol. The use of this solvent, with concomitant selection of the appropirate concentrations of the reactants, namely the aryl-trichloroacetate and the acrylonitrile, permit the direct conversion of the compound of formula (I) to the desired 3,5,6-trichloropyridin-2-ol without isolation of the compound of formula (I) from the reaction solution and its purification. This greatly simplifies the overall process from the technological point of view, as well as being economically advantageous. However, this procedure is not limited to the use of sulfolane as solvent and one may use another solvent from among those specified above for the cyclization of the compound of formula (I).

Thus, in accordance with a further preferred embodiment of the present invention, there is provided a process for producing 3,5,6-trichloropyridin-2-ol and alkali metal and alkaline earth metal salts thereof, which comprises the steps of:

reacting an aryl ester of trichloroacetic acid of the general formula $Cl_3CCOOAr$ wherein Ar is an optionally substituted aryl or heteroaryl radical, with acrylonitrile in a polar aprotic solvent as herein defined, in the presence of a catalytic amount of a metal selected from the main transition metal series and sub-groups IB and IIB or a salt or oxide of such metal, at a temperature from about 80° C. to about 180° C.;

cooling the reaction mixture to about 0° C. to 5° C. and charging it with anhydrous hydrogen chloride gas to a concentration of from about 10 to about 15% by weight of the total mixture; and heating the reaction mixture at a temperature of about 100° C. to about 180° C., preferably from about 125° C. to about 135° C.; and, if desired, coverting the 3,5,6-trichloropyrid-2-ol thus obtained to an alkali metal or alkaline earth metal salt thereof.

The desired product, 3,5,6-trichloropyridin-2-ol can be isolated from the reaction mixture as its sodium salt in the manner described hereinabove.

The various aspects of the present invention are illustrated in more detail in the following, non-limiting examples.

EXAMPLE 1

Preparation of 3,5,6-trichloropyridin-2-ol and its sodium salt

A solution of 40.0 g (0.137 mole) of phenyl 4-cyano-2,2,4-trichlorobutyrate and 190 ml of anhydrous sulfolane in a glass lined pressure reactor was cooled to 0° C. in an ice-water bath, and charged with dry HCl gas (28 g) at 5° C. by passing dry HCl gas therethrough. The reactor was closed and the reaction mixture heated with stirring at 125° C. for 5 hours. After cooling to ambient temperature, the HCl gas was vented off and a clear brown solution was obtained. GLC analysis of the resulting solution indicated a yield of 78% (±1%) of 3,5,6-trichloropyridin-2-ol. The solution was poured into water and extracted with several portions of methyl t-butyl ether. The combined extract was washed with water and then stirred for 1 hour with 150 ml of aqueous 13% sodium carbonate solution. A white solid formed in the aqueous phase and was filtered off, washed with methyl t-butyl ether and dried to give 23.0 g of 3,5,6-trichloropyridin-2-ol sodium salt. By acidifying the above sodium salt with dilute aqueous HCl, it was quantitatively converted into a white powder consisting of 3,5,6-trichloropyridin-2-ol, m.p. 170°–171° C. This substance was found to be identical in all respects with an authentic sample of the material.

EXAMPLE 2

Preparation of phenyl 4-cyano-2,2,4-trichlorobutyrate 51 g of phenyl trichloroacetate, 17.5 ml of acrylonitrile, 0.88 g of cuprous chloride, 0.3 g of pyridine hydrochloride and 80 ml of anhydrous sulfolane were charged into a glass lined pressure reactor and heated with stirring at 125° C. for 10 hours. After cooling to ambient temperature, the brown reaction mixture was found to be homogeneous but for undissolved copper salts. GLC analysis indicated a yield of 76% (±1.5%) of the title compound based on phenyl trichloroacetate. The title compound was isolated by pouring the reaction mixture into water, extracting with several portions of methyl t-butyl ether and washing the organic phase with water. Drying (MgSO$_4$) and subsequent removal of the combined organic extract by evaporation under reduced pressure yielded a light brown viscous oil which crystallized slowly on standing at ambient temperature. The resulting crystals were recrystallized from ether-petroleum ether (60–80) to give colorless needles of phenyl 4-cyano-2,2,4-trichlorobutyrate, m.p. 51.5°–52.5° C.;

IR (KBr): 1760 (CO) cm$^{-1}$;

$^1$H-NMR δ (CDCl$_3$; 360 MHz): 7.3 (multiplet, 5H), 4.9 (multiplet, 1H), 3.3 (ABX, $J_{AB}$=15.2Hz; $J_{AX}$=6.0Hz, 2H) ppm;

MS: M+291 (100%), 293 (98%), 295 (34%), 297 (3%) (Cl$_3$).

EXAMPLE 3

Preparation of 3,5,6-trichloropyridin-2-ol and its sodium salt 51 g of phenyl trichloroacetate, 17.5 ml of acrylonitrile, 0.88 g of cuprous chloride, 0.3 g of pyridine hydrochloride and 80 ml of anhydrous sulfolane were charged into a glass lined pressure reactor and heated with stirring at 125° C. for 10 hours. The reaction mixture was cooled to 5° C. and saturated with dry HCl gas (30 g) at that temperature. The reactor was closed and reheated with stirring at a temperature of 125° C. for 5 hours. After cooling to room temperature the resulting brown homogeneous solution was found to contain 14.1% of 3,5,6-trichloropyridin-2-ol (GLC analysis), which is equivalent to a 53.7% total yield based on phenyl trichloroacetate. The title product was isolated from the reaction mixture as described in Example 1.

EXAMPLE 4

Preparation of 3,5,6-trichloropyridin-2-ol and its sodium salt

The procedure described in Example 3 was repeated except that the phenyl trichloroacetate was replaced by 58.3 g of p-chlorophenyl trichloroacetate. The reaction afforded 3,5,6-trichloropyridin-2-ol in 51% yield based on the quantity of the p-chlorophenyl trichloroacetate.

EXAMPLE 5

Preparation of 3,5,6-trichloropyridin-2-ol and its sodium salt

The procedure described in Example 3 was repeated except that 60.6 g of p-nitrophenyl trichloroacetate were used instead of the phenyl trichloroacetate. The yield of 3,5,6-trichloropyridin-2-ol was found to be 54.3% based on the quantity of p-nitrophenyl trichloroacetate.

EXAMPLE 6

Preparation of 3,5,6-trichloropyridin-2-ol and its sodium salt

β-Naphthyl trichloroacetate (61.5 g, 0.212 mole), acrylonitrile (14.7 g, 0.265 mole), cuprous chloride (0.88 g) and sulfolane (100 ml) were heated in a closed reactor at 135° C. for 10 hours. After cooling the reactor to 5° C., its contents were charged with dry HCl gas (10% w/w). The reactor was closed and heated at 125° C. for 5 hours. After cooling to room temperature, the resulting homogeneous solution was found to contain 3,5,6-trichloropyridin-2-ol in a yield of 44.3% (by GLC analysis) based on the above quantity of β-naphthyl trichloroacetate.

EXAMPLE 7

Preparation of 3,5,6-trichloropyridin-2-ol and its sodium salt o-Methoxyphenyl trichloroacetate (57.4 g, 0.212 mole), acrylonitrile (14.7 g, 0.265 mole), cuprous chloride (0.88 g) and sulfolane (100 ml) were heated in a closed reactor at 135° C. for 10 hours. After cooling the reactor to 5° C., its contents were charged with dry HCl gas (10% w/w). The reactor was closed and heated for 5 hours at 125° C. The yield of 3,5,6-trichloropyridin-2-ol was found by GLC analysis to be 34% based on the above quantity of o-methoxyphenyl trichloroacetate.

EXAMPLE 8

Preparation of 3,5,6-trichloropyridin-2-ol and its sodium salt p-Tolyl trichloroacetate (54.0 g, 0.212 mole), acrylonitrile (14.7 g, 0.265 mole), cuprous chloride (0.88 g) and sulfolane (100 ml) were heated in a closed reactor at 135° C. for 10 hours. After cooling the reactor to 5° C., its contents were charged with dry HCl gas (10% w/w). The reactor was closed and heated for 5 hours at 125° C. The yield of 3,5,6-trichloropyridin-2-ol was found by GLC analysis to be 45% based on the above quantity of p-tolyl trichloroacetate.

EXAMPLE 9

Preparation of 3,5,6-trichloropyridin-2-ol and its sodium salt

A mixture of 3,5,6-trichloropyrid-2-yl trichloroacetate (73.0 g, 0.212 mole), acrylonitrile (14.7 g, 0.265 mole), cuprous chloride (0.88 g) and sulfolane (100 ml) was heated in a closed reactor at 125° C. for 18 hours. After cooling the reactor to 5° C., its contents were charged with dry HCl gas (10% w/w). The reactor was closed and heated for 5 hours at 125° C. The yield of 3,5,6-trichloropyridin-2-ol was found by GLC analysis to be 69.8% based on the above quantity of 3,5,6-trichloropyrid-2-yl trichloroacetate. Isolation of the product as described in Example 1 gave 63 g of 3,5,6-trichloropyridin-2-ol sodium salt.

The starting material 3,5,6-trichloropyrid-2-yl trichloroacetate was prepared as follows:

To a mixture of trichloroacetyl chloride (112 ml, 181.8 g, 1.0 mole) and 3,5,6-trichloropyridin-2-ol (198 g, 1.0 mole) in toluene (1.0 l) there was added, while stirring, pyridine (81 ml, 79 g, 1.0 mole). A white precipitate of pyridine hydrochloride formed immediately and was filtered off after stirring the reaction mixture for 1 hour. The toluene was removed by distillation under reduced pressure leaving a clear colorless liquid which crystallized at ambient temperature. Recrystallization of the solid material from light petroleum ether gave colorless prisms (294.4 g, 86%) of 3,5,6-trichloropyrid-2-yl trichloroacetate, m.p. 58°-60° C.;

IR(CHCl$_3$): 1800 cm$^{-1}$;

MS: M+ 341(48.6%), 343 (100%), 345 (79.8%), 347 (33.5%), 349 (5.4%) (Cl$_6$); M+-Cl$_3$CCO 197 (43.9%), 199 (42.8%), 201 (13.3%) (Cl$_3$).

EXAMPLE 10

Preparation of 3,5,6-trichloropyridin-2-ol and its sodium salt

Phenyl 4-cyano-2,2,4-trichlorobutyrate (44.25 g, 0.15 mole) was dissolved in 200 ml of acetonitrile in an enamel lined reactor, cooled to 0° C. and saturated with dry HCl gas. The reactor was heated for 8 hours at 125° C., then cooled to room temperature and the solvent was removed by distillation under reduced pressure. The residue was dissolved in methyl t-butyl ether (150 ml) and the resulting solution stirred at room temperature with a 13% w/w aqueous solution of sodium carbonate (200 ml) for 2 hours. The resulting suspension was filtered and the filter cake washed with methyl t-butyl ether to give 3,5,6-trichloropyridin-2-ol sodium salt, 14.4 g (44% yield).

EXAMPLE 11

Preparation of phenyl 4-cyano-2,2,4-trichlorobutyrate

Phenyl trichloroacetate (31.2 g, 97.1% purity, 0.126 mole) was mixed with acrylonitrile (10.5 ml, 8.46 g, 0.159 mole), pyridine hydrochloride 0.18 g and cuprous chloride (0.53 g, 5.3 mmole). The mixture was heated in a closed glass-lined reactor for 10 hours at 125° C.

Analysis indicated that the product contained 78.43% of the title compound, equivalent to 31.5 g (85.4% yield).

The product crystallized on standing.

EXAMPLE 12

Preparation of 3,5,6-trichloropyridin-2-ol

The crude (78.43%) phenyl 4-cyano-2,2,4-trichlorobutyrate product obtained in Example 11 (6.512 g, 0.0175 mole) was dissolved in a mixture of 7.8 g sulfolane and 7.8 g acetonitrile. The solution was cooled to 0°-5° C. and dry HCl gas was passed through the solution until the concentration of the dissolved HCl reached 20.4% by weight. The reactor was closed and the reaction mixture heated at 125° C. for 5 hours. The reactor was cooled down to 5° C. and the acetonitrile and excess HCl were distilled off under reduced pressure leaving 18.02 g of a brownish oil as residue.

Analysis of the residue indicated the presence of 15.8% by weight of 3,5,6-trichloropyridin-2-ol equivalent to 2.85 g (82% yield).

I claim:

1. Aryl 4-cyano-2,2,4-trichlorobutyrate of the general formula

NC—CHCl—CH$_2$—CCl$_2$—COOAr  (I)

wherein Ar is phenyl, methoxyphenyl, tolyl, naphthyl, pyridyl, phenyl substituted in at least one position by an electron-withdrawing substituent, naphthyl substituted in at least one position by an electron-withdrawing substituent, or pyridyl substituted in at least one position by an electron-withdrawing substituent.

2. A compound of claim 1 wherein Ar is phenyl, methoxyphenyl, tolyl, naphthyl or pyridyl.

3. A compound of claim 1 wherein Ar is phenyl naphthyl or pyridyl substituted in at least one of the para or ortho positions by at least one electron-withdrawing substituent.

4. A compound of claim 1, wherein said electron withdrawing substituent is Cl or NO$_2$.

5. A compound of claim 3, wherein said electron withdrawing substituent is Cl or NO$_2$.

6. Phenyl 4-cyano-2,2,4-trichlorobutyrate.

7. 3,5,6-Trichloropyrid-2-yl 4-cyano-2,2,4-trichlorobutyrate.

8. A process for producing 3,5,6-trichloropyridin-2-ol or alkali metal and alkaline earth metal salts thereof, which comprises cyclizing an aryl 4-cyano-2,2,4-trichlorobutyrate of the general formula NC—CHCl—CH$_2$—CCl$_2$—COOOAr  (I)

wherein Ar is phenyl, methoxyphenyl, tolyl, naphthyl, pyridyl, phenyl substituted in at least one position by an electron-withdrawing substituent, naphthyl substituted in at least one position by an electron withdrawing substituent or pyridyl substituted in at least one position by an electron withdrawing substituent, by heating the compound of formula (I) at a temperature from about 100° C. to about 180° C., in an inert organic solvent selected from the group consisting of C$_2$-C$_5$ alkylcyanides, benzonitrile, dialkyl sulfones, alkyl aryl sulfones, alkyl aralkyl sulfones and cyclic sulfones, in the presence of anhydrous hydrogen chloride in amounts from 0.1 to 2 parts by weight per 1 part by weight of compound of formula (I) or converting the 3,5,6-trichloropyrid-2-ol thus obtained to an alkali metal or alkaline earth metal salt thereof.

9. A process according to claim 8 wherein Ar is phenyl, methoxyphenyl, tolyl, naphthyl or pyridyl.

10. A process according to claim 8 wherein Ar is phenyl, naphthyl or pyridyl substituted in at least one of the para or ortho positions by at least one electron-withdrawing substituent.

11. A process according to claim 8, wherein the cyclization of the compound of formula (I) is carried out at a temperature from about 125° C. to about 135° C.

12. A process according to claim 8, wherein the amount of anhydrous hydrogen chloride is from 0.4 to 1.0 parts by weight per 1 part by weight of the compound of formula (I).

13. A process according to claim 8, wherein the solvent is sulfolane.

14. A process according to claim 8, wherein the product is isolated from the reaction mixture, as the sodium salt, by extraction with a saturated aqueous sodium carbonate solution.

15. A process according to claim 8, wherein said electron withdrawing substituent is Cl or No$_2$.

16. A process according to claim 10, wherein said electron withdrawing substituent is Cl or NO$_2$.

17. A process for producing 3,5,trichloropyrridin-2-ol or alkali metal and alkaline earth metal salts thereof, which comprises the steps of:

reacting an aryl ester of trichloracetic acid of the general formula Cl$_3$CCOOAr wherein Ar is phenyl, methoxyphenyl, tolyl, naphthyl, pyridyl, phenyl substituted in at least one position by an electron-withdrawing substituent, naphthyl substituted in at least one position by an electron-withdrawing substituent, or pyridyl substituted in an at least one position by an electron-withdrawing substituent, with acrylonitrile in an inert organic solvent selected from the ground consisting of C$_2$-C$_5$-alkylcyanides, benzonitrile, dialkyl sulfones, alkyl aryl sulfones, alkyl aralkyl sulfones and cyclic sulfones, in the presence of a catalytic amount of a metal selected from the main transition metal series and sub-groups 1B and IIB or a salt or oxide of such metal, at a temperature from about 80° to about 180° C.;

cooling the reaction mixture to about 0° C. to 5° C. and charging it with anhydrous hydrogen chloride gas to a concentration from about 10 to about 15% by weight of the total mixture; and heating the reaction mixture at a temperature of about 100° C. to about 180° C.;

or converting the 3,5,6-trichloropyridin-2-ol thus obtained to an alkali metal or alkaline earth metal salt thereof.

18. A process according to claim 17 wherein Ar is 3,5,6-trichloropyrid-2-yl.

19. A process according to claim 17 wherein sulfolane is used as the inert organic solvent.

20. A process according to claim 17 wherein the product is isolated from the reaction mixture, as the sodium salt, by extraction with a saturated aqueous sodium carbonate solution.

* * * * *